(12) United States Patent
Marbach

(10) Patent No.: US 7,139,076 B1
(45) Date of Patent: Nov. 21, 2006

(54) STABLE OPTICAL DIFFUSE REFLECTION MEASUREMENT

(76) Inventor: Ralf Marbach, Kumpulankaari 1, 90650 Oulu (FI)

( * ) Notice: Subject to any disclaimer, the term of this patent is extended or adjusted under 35 U.S.C. 154(b) by 417 days.

(21) Appl. No.: 10/636,639

(22) Filed: Aug. 8, 2003

Related U.S. Application Data

(60) Provisional application No. 60/401,868, filed on Aug. 9, 2002.

(51) Int. Cl.
 *G01N 21/47* (2006.01)
(52) U.S. Cl. ..................................................... 356/446
(58) Field of Classification Search ...................... None
 See application file for complete search history.

(56) References Cited

U.S. PATENT DOCUMENTS 4,884,891 A * 12/1989 Borsboom .................. 356/446
5,986,770 A * 11/1999 Hein et al. .................. 356/446
6,573,984 B1 * 6/2003 Jung et al. .................... 356/73
6,795,195 B1 * 9/2004 Barbour et al. ............. 356/446

* cited by examiner

*Primary Examiner*—Michael P. Stafira

(57) ABSTRACT

Apparatus and methods for stable and reproducible optical diffuse reflection measurement are described. Light sources and photodetectors are used such that at least two points of light entry and at least two points of light exit are established on the surface of the sample. The light sources are modulated and the detector outputs are demodulated such that the signals associated with the at least four optical measurement beams are individually detected. The signals are processed such that all instabilities generated at the surface of the sample are canceled out. In effect, the accuracy of the measurement is increased by having only the deeper layers of the sample contribute to the result. The geometry of the probe can be optimized for specific sampling depths and for specific measurement applications. Spectroscopic referencing can be eliminated since instabilities of light emission and detection are also canceled out.

20 Claims, 3 Drawing Sheets

STABLE OPTICAL DIFFUSE REFLECTION MEASUREMENT

CROSS-REFERENCE TO RELATED APPLICATIONS

This application is entitled to the benefit of Provisional Patent Application No. 60/401,868 filed 2002 Aug. 9.

FIELD OF THE INVENTION

The invention relates to apparatus and methods for performing optical diffuse reflection measurements.

BACKGROUND OF THE INVENTION

Optical diffuse reflection is a measurement technique used to probe the optical properties of turbid, i.e., scattering, samples. The technique is especially popular in the visible (VIS) and near-infrared (NIR) regions of the electromagnetic spectrum, where hardware is relatively cheap, and typical applications include industrial process control measurements, e.g., measurement of humidity in paper, and biomedical measurements, e.g., measurement of fat concentration in the skin. Major advantages of diffuse reflection over other optical sampling techniques include (a) the minimal need for sample preparation, because many practically important types of samples are scattering by nature, and (b) the possibility to perform measurements on bulky samples.

Most applications require spectroscopic measurements, i.e., diffuse reflection is measured at multiple optical wavelengths, $\lambda_i (i=1,2 \ldots)$, and then so-called multivariate calibration is used to determine an algorithm that transforms the measured spectrum, $S(\lambda_i)$ [Watt], into a single user-desired output number. The optimal algorithm to transform the multivariate input data, $S(\lambda_i)$, into the desired analytical result is the so-called specific multivariate Wiener filter. (In practice, the unit of $S(\lambda)$ varies with the instrument hardware and can also be, e.g., [Volt], [Ampere], [Coulomb], or [Digital Number], but all of these are proportional to detected optical power so without loss of generality, we will consistently use [Watt] here.) Data from multivariate measurements usually have much better accuracy than univariate data, because noise that is correlated between different inputs can be subtracted out in the algorithm. This statement has recently been cast into quantitative form by deriving the formula for the signal-to-noise ratio of a multivariate measurement, $SNR_X = s/n_{eff}$, where s is the root-mean-square (rms) signal, and $$n_{eff} = \frac{1}{\sqrt{g^T \cdot N_x^{-1} \cdot g}} \qquad \text{Eq. (1)}$$

is the rms effective noise of the multivariate data. Here, s and $n_{eff}$ are measured in some user-defined and application-specific [concentration unit] of the property or analyte of interest, e.g., [gram/Liter]; $N_x$ the covariance matrix of the multivariate noise in the measured data, in some [measurement unit squared], e.g., [Volt squared]; and g the so-called response vector, in [measurement unit/concentration unit]. For details, see R. Marbach, *On Wiener filtering and the physics behind statistical modeling*. Journal of Biomedical Optics 7, 130–147 (2002) and also, *A New method for multivariate calibration*, J. Near Infrared Spectrosc. 13, 241–254 (2005), where the latter paper is application-oriented and straightforward to read. High measurement accuracy is equivalent to low effective noise, $n_{eff}$, which, for a given rms signal s, is equivalent to a high $SNR_X$. Equation (1) will repeatedly be referred to below, because it provides the motivation for much of the following. Commercially successful analytical measurements based on multivariate data generally achieve $SNR_X > 3$.

A disadvantage of the diffuse reflection technique is the lack of a simple formula that could provide an exactly linear relationship between the measured spectrum, $S(\lambda)$, and the quantity of interest, e.g., concentration of a specific component in the sample. Loosely speaking, nothing as simple as the Lambert-Beer law is available. In practice, however, this is not a severe limitation because often, only small changes around a stable, average sample are observed and these small changes behave approximately linear. Linearity can be further improved by applying software pre-processing steps to the measured spectrum, $S(\lambda)$, before feeding it into the calibration algorithm. The details of the pre-processing depend on the details of the application and used hardware and, to some extent, historical preferences. Various options are available and have been discussed in the pertinent literature. The most commonly used pre-processing steps include taking the logarithm, $-\log\{S(\lambda)/\text{Watt}\}$, or when a spectrum $S_R(\lambda_i)$ from a reference standard is available, $-\log\{S(\lambda_i)/S_R(\lambda_i)\}$; and mean centering; see, e.g., Peter R. Griffiths, *Letter: Practical consequences of math pre-treatment of near infrared reflectance data*: log (1/R) vs F(R), J. Near Infrared Spectrosc. 3, 60–62 (1995). The popularity of taking the logarithm is also directly explained by Eq.(1): while not necessarily optimal at linearizing the spectral signal, the logarithm does perform a virtually perfect job at subtracting out spectral noises, and thus usually outperforms other, competing methods in the resulting signal-to-noise ratio, $$SNR_X = s\sqrt{g^T N_x^{-1} g} . \qquad \text{Eq. (2)}$$

Most diffuse reflection measurements in use today are ratiometric measurements, i.e., the optical signal from the sample, $S(\lambda)$, is ratioed by the optical signal received from a reflectance standard, $S_R(\lambda)$ [Watt], to produce the diffuse reflection spectrum, $R(\lambda) = S(\lambda)/S_R(\lambda)$, or the absorbance-equivalent, $-\log\{S(\lambda)/S_R(\lambda)\}$, after the most typical pre-processing. This ratio operation is known as "spectroscopic referencing" and instruments often contain a built-in reflectance standard that is moved in and out of the measurement position before or after the sample measurement. From the point of view of qualitative interpretation of the measured spectra, the purpose of referencing is to isolate the spectral signature of the sample by ratioing out the spectral characteristics of the instrument; thus, reflectance standards usually have as flat a reflection spectrum, $S_R(\lambda) \cong \text{const}(\lambda)$, as possible over the wavelength range of interest. From the point of view of accuracy of a quantitative measurement, referencing decreases the spectral noise in the larger eigenfactors of the covariance matrix of the spectral noise, $N_x$, at the expense of a slight noise increase in the smaller eigenfactors (cmp. Marbach 2002). Since the spectral signal usually resides in the larger eigenfactors, referencing usually results in a net improvement of $SNR_X$ a.k.a. measurement accuracy.

Most diffuse reflection probes in use today are based on bifurcated fiber optic cables, in which illumination and collection fibers coming from two separate arms of the cable are combined and arranged in close proximity at the distal end of the cable (the probing end). In the VIS range, plastic fibers can be used, but glass fibers are used in most designs. All three ends of the cable are usually ground flat and polished after the fibers have been fixed into place. The total number of fibers used in typical probes varies, from two to several hundred, and various geometries with different relative merits exist and are in common use. One of the most important design parameters of a fiber probe is lateral distance, i.e., the (average) distance between the illumination fiber(s) and the collection fiber(s) measured along the surface of the sample. Lateral distance, along with the optical properties of the sample, largely determines the throughput efficiency of the probe (fraction of the light that is collected back) as well as the average penetration depth of the measurement light into the sample. One important advantage of fiber probes is the low sensitivity to surface (a.k.a. Fresnel) reflections at the sample surface. Surface reflections generally do not carry desired information about the sample and are usually detrimental to measurement accuracy. Non-fiber probes, which are based on conventional optical elements like windows, lenses, mirrors, beam-splitters, etc.; can achieve higher throughput efficiency than fiber probes but are generally more expensive and harder to use; for an example of a very high-throughput, non-fiber probe, see R. Marbach and H. M. Heise, *Optical Diffuse Reflectance Accessory for Measurements of Skin Tissue by Near-Infrared Spectroscopy*, Appl. Optics 34, 610–621 (1995). Because the areas of light entry into the sample, and light exit from the sample, are usually spatially-overlapping in non-fiber probes, surface reflections are usually a bigger problem than in fiber probes.

A dominant problem in many diffuse reflection measurements is instability generated by various physical effects located at or near the surface of the sample. Physical reasons include various microscopic, yet optically relevant, changes due to, e.g., dust, scratches in the glass of the probe, changes in the contact pressure between the probe and the sample, or slow variations of the optical properties of the surface layer of the sample due to changes in the ambient. We use the terms surface instabilities or surface noise to describe all of these effects, regardless of their physical origin. An example of an application suffering from surface instabilities is the diffuse reflection measurement of the scattering coefficient, $\mu_S$, of human skin, which has been proposed as an indicator measurement closely correlated to changes in the blood glucose concentration. Experiments have shown that +1 mmol/Liter of change in blood glucose concentration causes a relatively large change of about $\Delta\mu_S/\mu_S \approx -0.3\%$ in in-vivo skin, see L. Heinemann et al., *Noninvasive Glucose Measurement by Monitoring of scattering Coefficient During Oral Glucose Tolerance Tests*, Diabetes Technology & Therapeutics 2, 211–220 (2000). Unfortunately, however, the instability of the measurement turned out to be much larger. Tests on healthy volunteers suffered from up to 5% of magnitude of drift over a measurement time of a few hours, in spite of the fact that the fiber probes were glued to the abdomen and volunteers were lying in bed as still as possible. From the time profiles of the drift, the authors concluded that accumulation of moisture underneath the probe due to the ever-present, unnoticeable slight sweating ("transepidermal water loss") was a major reason for the observed drift. Sweating is a typical surface instability effect in many biomedical measurements.

The following paragraph will introduce notation used throughout the remainder of this document.

The vast majority of diffuse reflection probes in use today employ only a single 'measurement beam' through the sample, i.e., there is only a single 'point of light entry' into the sample and only a single 'point of light exit.' The phrase 'point of entry' here is used in a general sense meaning 'sample surface area of light entrance of a measurement beam,' and ditto for light exit. The definition of 'measurement beam' goes hand in hand with the definitions of entry and exit point and is as follows: a measurement beam is composed of measurement light that has probed the sample and is individually detected by the measurement instrument. For example, in the case of a simple fiber optic probe with only one illumination and one pickup fiber, both butted against the sample surface, the point of light entry is the distal face of the core of the illumination fiber and the point of light exit is the distal face of the core of the pickup fiber. Between the two and through the sample extends the one measurement beam. In the following, we will call this a 1×1 probe, meaning, 1 entry point ×1 exit point. Assuming the probe contained, say, 200 illumination fibers illuminated by one light source and 30 pickup fibers guiding light to one photodetector, then this would still be a 1×1 probe but now with the single point of light entry consisting of 200 circular areas and the single point of light exit consisting of 30 circular areas. However, if the 200 illumination fibers were divided into two groups of, say, 100 fibers each and illumination of the two groups was modulated and the electrical output of the single photodetector was demodulated such that the signals from the two groups were detected individually, e.g., by illuminating the two groups in alternating sequence, then there would be two points of light entry with 100 circles each and still one point of light exit with 30 circles. This last example is called a 2×1 probe and forms two measurement beams through the sample. As a theoretical maximum, a probe with 200 illumination fibers and 30 pickup fibers could establish 200 points of entry and 30 points of exit and could form a 200×30 probe, but that would require that 200×30=6000 measurement beams be individually modulated and detected, which is not feasible. In practice, multiple fibers are combined and the vast majority of probes today are 1×1 probes. Fibers are usually combined optically by forming fiber bundles, but sometimes, pickup fibers are combined electrically by adding the electrical signals from several photodetectors or are combined in software by effectively adding their signals after A/D conversion. In many cases, the one measurement beam of a 1×1 probe is spectroscopically broken down into multiple, individually detected signals from different wavelength bands, but in the discussed sense of beam geometry through the sample, these are still 1×1 probes. Lastly, it is not necessary that points of light entry and light exit are spatially separate from each other, but rather, they can overlap or even be identical, which is common in non-fiber probes.

A few probes have been built, mostly for research purposes, that use either multiple entry points or multiple exit points. The principal application here is the measurement of the so-called spatially resolved diffuse reflection spectrum, $R(\lambda;r)$, where r[mm] is lateral distance. For example, the fiber probe used in the experiments described by Heinemann et al. 2000 consisted of a single illumination fiber and eight pickup fibers guided to form the input slit of an imaging spectrograph, thereby establishing a single point of entry and potentially eight points of exit (assuming that the eight signals had not been combined in software). As already stated above, however, the vast majority of diffuse reflection probes in use today are 1×1 probes, or are arrangements of multiple (independent) 1×1 probes dispersed over a spatially extended surface area of the sample for some type of imaging purpose.

A few more remarks concerning notation are necessary. First, we stress that the notation introduced above, viz., "$N_{in} \times N_{out}$ probe;" refers to more than just the number of light entry points ($N_{in}$) and light exit points ($N_{out}$). The notation also implies that measurement beams are established between all entry and exit points, i.e., that a total of ($N_{in} \times N_{out}$)-many measurement beams are individually detected by the hardware. Next, in the following, two measurement beams are called signal-redundant whenever their measurement results are identical under the assumption of a spatially uniform sample. For example, in the hypothetical example of the 200×30 fiber probe above, many of the 6000 beams would be signal redundant because the geometry of their fibers and their lateral distance would be identical. Further, the term diffuse reflection is commonly used whenever the entry and exit points are located close to each other and on the same macroscopic side of the sample, as opposed to other terms like diffuse transmittance etc., which are commonly used when the two are located on opposite sides of the sample. Schmitt and Kumar, however, have pointed out that there is no clear-cut distinction between reflection and transmission whenever the sample is turbid, because every situation is a mixture of both, so to speak, see J. M. Schmitt and G. Kumar, *Spectral Distortions in Near-Infrared Spectroscopy of Turbid Materials*, Appl. Spectrosc. 50, 1066–1073 (1996). The authors point out that at small lateral distances, reflection dominates because an increase in the scatter coefficient, $\mu_S$, [mm$^{-1}$], of the sample will cause an increase in the detected power, S($\lambda$) [Watt]; however, at large lateral distances the measurement will actually behave like a transmission set-up, because an increase in $\mu_S$ will cause a decrease in S($\lambda$). Here, we use the term diffuse reflection regardless of the direction and magnitude of the change in S($\lambda$) caused by a change in $\mu_S$, and regardless of whether or not the sample actually has a macroscopic, planar surface and how the points of entry and exit are oriented with respect to the sample. Also, we use the term diffuse reflection even if the measurement light, or part of it, is spatially coherent (e.g., from a superluminescent LED with single transverse mode) or time-coherent (e.g., from a laser with single longitudinal mode). In summary, we use the term diffuse reflection whenever a turbid sample is probed with an optical measurement beam that makes use of, or is subject to, scattering inside the sample.

SUMMARY OF THE INVENTION

Stability and reproducibility of optical diffuse reflection measurements are improved by (a) providing at least two points of light entry and at least two points of light exit on the surface of the sample; (b) detecting at least four measurement beams individually; and (c) processing the at least four detected signals in such a way that all surface instabilities are effectively ratioed out between at least two, mutually-referencing measurement beams. In effect, the amplitude of the desired measurement signal is decreased because contributions generated in the surface layer of the sample are subtracted out, but the signal-to-noise ratio of the measurement of the deeper layers is increased because more noise is substracted out than signal. The at least four measurement beams through the sample can be established in a multitude of ways through design or mode of operation of the diffuse reflection probe. Several preferred embodiments are described in detail below.

In addition to eliminating surface instabilities, several other significant advantages are realized. First, the instability of light emission of each light source and the instability of light detection of each detector is also ratioed out, as is the light-guiding instability of each and every optical component guiding light to and from the sample. Second, the geometry of the probe can be designed to achieve a desired sampling depth into the sample and to optimize the multivariate signal-to-noise ratio, i.e., the $SNR_X$ in Eq.(2); for a particular measurement application, see details below. And third, spectroscopic referencing can be eliminated.

The disclosed apparatus and methods improve the stability and reproducibility of optical diffuse reflection measurements by orders of magnitude over the current state of the art. Important application areas include industrial process-control and biomedical monitoring in the VIS and NIR spectral ranges.

DETAILED DESCRIPTION OF THE INVENTION

In the following, points of light entry will be denoted by capital letters (A, B, . . . ) and points of light exit will be denoted by Latin numerals (i, ii, . . . ). Combinations will be used to denote optical measurement beams, e.g., Bii denotes the beam extending between entry point B and exit point ii, and $S_{Bii}$ [Watt] denotes the amplitude of its optical signal as well as of the associated electrical, analog or digital, signals.

Figure 1A:
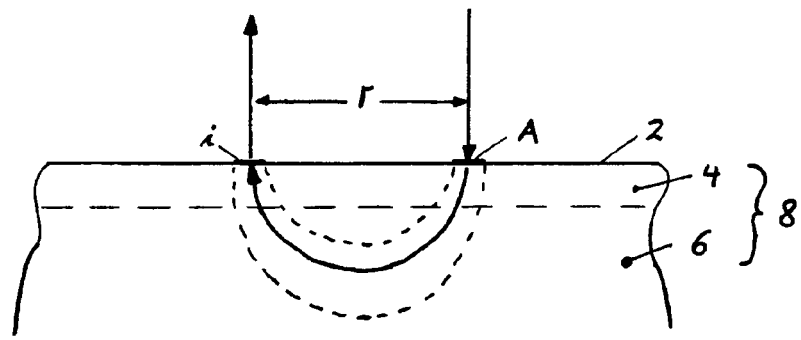
FIG. 1A shows a schematic cross-section of an optical measurement beam in a diffuse reflection measurement.

FIG. 1A shows a schematic cross-sectional view of a diffuse reflection measurement beam. The optical measurement beam enters at entry point A through the surface 2 and surface layer 4 into the bulk layer 6 of a turbid sample 8, and leaves through exit point i. Inside sample 8, light is randomly scattered and a small fraction of the photons launched at A will be collected at i. Depending on the geometry of A and i and the wavelength-dependent scattering and absorption characteristics of the sample, an effective cuvette is formed inside sample 8, defined as that volume of the sample that is effectively probed by beam Ai (usually a banana-shaped path). Different mathematical models can be used to describe the scattering in more or less detail, see the pertinent literature. In many cases, the diffusion equation can be used, with the rule of thumb that, if entry and exit points are separated by a lateral distance of r[mm], then penetration depth, L, and lateral distance are related by, L≅r/2. The amount of light collected at i decreases rapidly with increasing r and in the VIS and NIR wavelength ranges, r<5 mm is typical.

The entry and exit points schematically shown in FIGS. 1A–E can be realized in different ways using, e.g., LEDs and photodetectors located in close proximity to surface 2, or optical fibers contacting surface 2, or lenses or mirrors focussed at surface 2. Several preferred embodiments will be described in detail below. For now, we focus on the basic 2×2 geometry of the disclosed matter in order to explain the principal advantages of the invention first. We start with the assumption that only a single optical measurement wavelength (λ) is used, e.g., that only a single type of LED and single type of photodetector are used. 'Single wavelength' here does not necessarily mean that light sources emit a spectrally pure, narrow emission line, but rather, that the measurement is spectrally univariate, i.e., is not spectroscopically resolved into several signals from different λ-bands.

Figure 1B:
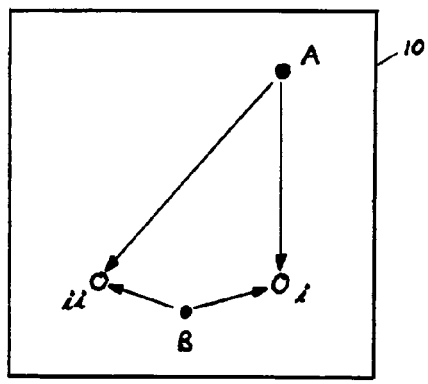
FIG. 1B shows a schematic top view of a 2×2 diffuse reflection probe.

In a nutshell, the idea behind this invention is to have the surface layer underneath each entry and exit point be penetrated by at least two mutually-referencing beams. A schematic top view (looking down at surface 2) of the basic 2×2 geometry of the invention is shown in FIG. 1B. Two entry points A and B and two exit points i and ii are located within the outline of a probe housing 10. Four measurement beams (indicated as arrows) are individually detected by the hardware of the instrument (not shown) and diffuse reflectance, R, is computed, e.g., as a ratio of two ratios:

$$R = \frac{\frac{S_{Aii}}{S_{Ai}}}{\frac{S_{Bii}}{S_{Bi}}}. \qquad \text{Eq. (3)}$$

(Equation (3) is an example of the so-called explicit-ratio method; another signal processing method that can also be applied is the so-called Wiener-filter method. Both of these methods will be described in detail below. Modern electronics, and especially, microprocessor technology, can easily provide the computing power necessary for either one. Since the explicit-ratio method is simpler to describe in the case of the basic 2×2 geometry, we start with it.) Two beams are called mutually-referencing whenever they share the same entry or exit point. For example, in Eq.(3), $S_{Aii}$ references with $S_{Ai}$ and with $S_{Bii}$, but not with $S_{Bi}$. The resulting benefit is best explained by writing the amplitude of optical beam Aii as, $$S_{Aii} = L_A \cdot TS_{A(ii)} \cdot TB_{Aii} \cdot TS_{ii(A)} \cdot D_{ii} \qquad \text{Eq.(4)}$$

and ditto for the other beams. Here, $L_A$ is the optical power [Watt] irradiating the sample at A; $TS_{A(ii)}$ the transmission through surface layer 4 located underneath A (probed by ii); $TB_{Aii}$ the transmission through bulk layer 6 located between A and ii; $TS_{ii(A)}$ the transmission through surface layer 4 located underneath ii (probed by A); and $D_{ii}$ the responsivity of the photodetector located at ii (dimensionless for the purposes of this discussion because we previously defined $S_{Aii}$ to be measured in [Watt]). Dissecting the optical beams into three segments (surface→bulk→surface) and assigning transmission numbers is arbitrary, of course, but valid for the purposes of this discussion. Inserting into Eq.(3) yields $$R = \frac{\frac{S_{Aii}}{S_{Ai}}}{\frac{S_{Bii}}{S_{Bi}}} = \frac{\frac{L_A \cdot TS_{A(ii)} \cdot TB_{Aii} \cdot TS_{ii(A)} \cdot D_{ii}}{L_A \cdot TS_{A(i)} \cdot TB_{Ai} \cdot TS_{i(A)} \cdot D_i}}{\frac{L_B \cdot TS_{B(ii)} \cdot TB_{Bii} \cdot TS_{ii(B)} \cdot D_{ii}}{L_B \cdot TS_{B(i)} \cdot TB_{Bi} \cdot TS_{i(B)} \cdot D_i}} \cong \frac{\frac{TB_{Aii}}{TB_{Ai}}}{\frac{TB_{Bii}}{TB_{Bi}}} \qquad \text{Eq. (5)}$$

because $$TS_{A(ii)} \cong TS_{A(i)} \qquad \text{Eq.(6A)}$$

$$TS_{B(ii)} \cong TS_{B(i)} \qquad \text{Eq.(6B)}$$

$$TS_{ii(A)} \cong TS_{ii(B)} \qquad \text{Eq.(6C)}$$

$$TS_{i(A)} \cong TS_{i(B)} \qquad \text{Eq.(6D)}$$

Thus, all surface instabilities and all instabilities of light emission and detection are ratioed out, and the result R is dependent only on the optical properties of the deeper layers of the sample. Since the properties of the deeper layers are usually more stable than those at the surface, the accuracy a.k.a. $SNR_X$ of the measurement is usually improved. Spectroscopic referencing is no longer necessary because light source instabilities and detector instabilities are also canceled out. Only in a few, research-type applications where basic knowledge about the material properties of a sample is gathered, can spectroscopic referencing (i.e. using a separate, known reflectance standard) provide an additional advantage.

In any diffuse reflection measurement the maximum penetration depth is limited by the scattering characteristics of the sample and the hardware noise-floor. In a 2×2 (or higher-order) probe there is also a user-controlled mechanism which can be used to limit the minimum depth with which to effectively probe the sample. For example, the better the two beams in each of Eqs.(6A–D) overlap spatially on, and close to, surface 2 the more effective the cancellation of surface noise and the more stable the result, Eq.(3), will be. The effective depth of surface layer 4 is determined by the extent of the three-dimensional beam overlap inside sample 8. In general, a tradeoff exists between effectiveness of cancellation and remaining signal strength. This can be used to achieve a desired minimum effective probing depth into the sample. For example, by locating the entry and exit points in FIG. 1B in such a way that the angle between connection lines A-ii and A-i is further decreased, the effective thickness of surface layer 4 underneath A will increase because the effective cuvettes formed by beams Aii and Ai will be overlapping for a longer, shared optical pathlength. Corresponding statements hold for all entry and exit points, e.g., the effective depth of surface layer 4 underneath B, which may be different from that underneath A. Accurate estimates of the effective depth of the surface layer underneath each entry or exit point are possible by detailed numerical modeling of the scattering in the sample, which can take even small details into account like, e.g., non-uniform spatial distribution of irradiance.

In FIG. 1B, the pathlength of the effective measurement cuvette through bulk layer 6, which gives rise to the result, Eq.(3), is determined by the difference between the geometrical shapes of beams Aii and Ai, whereas beams Bii and Bi do not contribute. This is, the ratio, $S_{Aii}/S_{Ai}$, or rather its absorbance-equivalent, $-\log(S_{Aii}/S_{Ai})$, carries the desired information about the optical properties of bulk layer 6. Beams Bii and Bi, on the other hand, with their lateral distances set equal, are signal-redundant, i.e., their ratio, $S_{Bii}/S_{Bi} \cong 1$, does not carry any desired information but, in FIG. 1B, is merely used to ratio out surface instabilities underneath points ii and i as well as all detector instabilities. Setting the lateral distances to be equal, however, is not necessary in practice. What is preferred in practice depends on what is to be measured.

As a first and somewhat surprising example, assume that beams Bii and Bi are signal-redundant and that beams Aii and Ai are also made signal-redundant, e.g., by moving entry point A in FIG. 1B further to the left until the connection line A-B is orthogonal to connection line ii-i. The result of Eq.(3) is then, $R \cong 1$, which does not seem to be very interesting at first glance. However, the small deviation from the ideal R=1 is now a very reliable indicator of the spatial non-uniformities of bulk layer 6, and of bulk layer 6 only, i.e., unaffected by any non-uniformities of surface layer 4 or any surface noise for that matter. A practical application of this type of probe is a simple and rugged device for the detection of spatial non-uniformities in the human dermis, e.g., for skin cancer detection. A miniaturized, battery-powered probe of this kind can be built from, e.g., LEDs and Silicon photodiodes, and could be manually scanned across suspected skin areas. An acoustic output signal, which is silent at R=1 and increases in volume with increasing deviation from R=1, is preferred. Making the lateral distance of beams Aii and Ai different from the lateral distance of beams Bii and Bi supports a user's ability to even make a rough estimate of the size of a detected non-uniformity, by moving the probe slightly back and forth across it and listening to the sound effect created when unbalancing the different pairs of mutually-referencing beams.

Figure 1C:
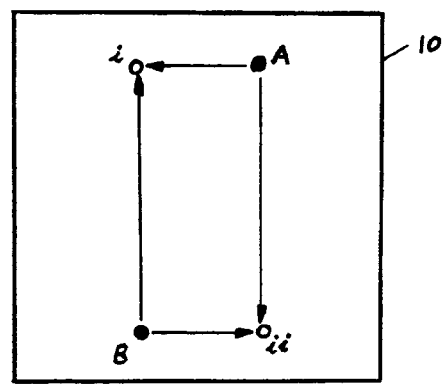
FIG. 1C shows a schematic top view of another 2×2 diffuse reflection probe preferred in the case of measurement of scatter coefficient.

As another example, assume the scatter coefficient, $\mu_S$ [mm$^{-1}$], of bulk layer 6 was to be measured. (In practice, what is more often measured than $\mu_S$ is the so-called reduced scattering coefficient, $\mu'_S = (1-g)\mu_S$, where g is the so-called anisotropy factor, which is a dimensionless number in the range, 0<g<1, and typically around, $g \cong 0.8$. For the purposes of this discussion, we do not strictly differentiate between $\mu_S$ and $\mu'_S$ and when talking about "measuring the scatter coefficient," we refer to sample scattering in general, regardless of whether the sample consists of several different physical layers or not and whether the scattering is mathematically described by one parameter, $\mu'_S$, or two parameters, $\mu_S$ and g, or in any other way. The pertinent literature contains detailed explainations of, and user guides to, the different mathematical models of scattering and the different parameters used.) A preferred arrangement of the basic 2×2 geometry for this application is depicted in FIG. 1C. Referring back to the discussion about transmission dominated and reflection dominated beams (Schmitt and Kumar 1996), the lateral distances of the four beams in FIG. 1C are chosen such that beams Aii and Bi are transmission dominated and beams Ai and Bii are reflection dominated. (For completeness, we mention that some of the beams could also be on the border between the two regions.) An increase in the scatter coefficient, $\mu_S$, then causes a decrease in ratio $S_{Aii}/S_{Ai}$ (transmission/reflection dominated) and an increase in ratio $S_{Bii}/S_{Bi}$ (reflection/transmission dominated). Thus, the signals of the two ratios add up in phase in Eq.(3), so to speak, and create a large, desired measurement effect, $\Delta R/R$, due to $\Delta\mu_S/\mu_S$. Furthermore, if the wavelength of the measurement light ($\lambda$) is chosen such that the reduced scattering coefficient, $\mu'_S$, is much larger than the absorbance coefficient, $\mu_A$, of the sample, then the effect of any $\Delta\mu_A/\mu_A$ on the measured $\Delta R/R$ will be negligible. Fortunately, for many of the practically important types of samples, the condition, $\mu'_S(\lambda) \gg \mu_A(\lambda)$, is fulfilled in the VIS and NIR ranges.

Figure 1D:
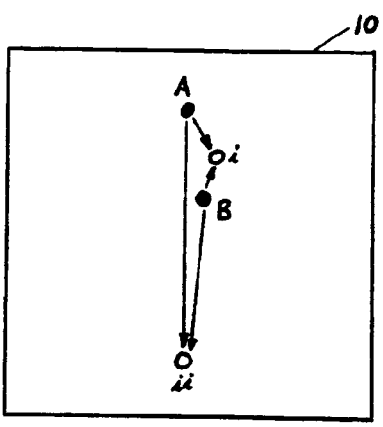
FIG. 1D shows a schematic top view of another 2×2 diffuse reflection probe preferred in the case of measurement of absorbance coefficient.

As another example, assume that the absorbance coefficient, $\mu_A$[mm$^{-1}$], of bulk layer 6 was to be measured and that changes in $\mu_S$ were considered undesired interference. In this case, a preferred arrangement of the basic 2×2 geometry is shown in FIG. 1D. Here, the bulk of the effective measurement cuvette is created by the difference between the geometrical shapes of beams Aii and Bii, whereas beams Ai and Bi are almost signal-redundant. The lateral distances are chosen such that beam Aii is transmission dominated, beam Bii can be freely optimized for a desired sampling depths, and beams Ai and Bi are close to each other and close to the transition between transmission and reflection dominance, see details below. The bulk of the desired absorbance-equivalent signal, $$\frac{\partial}{\partial\mu_A}(-\log\{R\}) \cdot \Delta\mu_A,$$

is thus from $$\frac{\partial}{\partial\mu_A}\left(-\log\left\{\frac{S_{Aii}}{S_{Bii}}\right\}\right),$$

but this ratio is also affected by an undesired, often larger scatter effect, $$\frac{\partial}{\partial\mu_S}\left(-\log\left\{\frac{S_{Aii}}{S_{Bii}}\right\}\right).$$

This scatter effect can be canceled, however, and the desired $$\frac{\partial R}{\partial\mu_S} \cong 0$$

be achieved, by judiciously choosing the lateral distances, r, of the other two beams, Ai and Bi. Since the lateral distances of these beams are short and in the transition region, where $$\frac{\partial^2 S}{\partial r \partial\mu_S}$$

is a steep function of r, a slight difference in the lateral distances, $r_{Ai}=r_{Bi}(1+\epsilon)$ with $|\epsilon|\ll 1$, can be used to create a relatively large and canceling second scatter effect, $$\frac{\partial}{\partial\mu_S}\left(-\log\left\{\frac{S_{Bi}}{S_{Ai}}\right\}\right),$$

whereas the absorbance effect of these two beams will be negligible, $$\frac{\partial}{\partial \mu_A}\left(-\log\left(\frac{S_{Bi}}{S_{Ai}}\right)\right) \cong 0.$$

As usual in ill-posed measurements, careful fine-tuning is required when defining the values of $r_{Ai}$ and $r_{Bi}$ in order to achieve good cancellation of the scatter effects, and this can best be achieved experimentally, rather than by relying on numerical simulations.

Figure 1E:
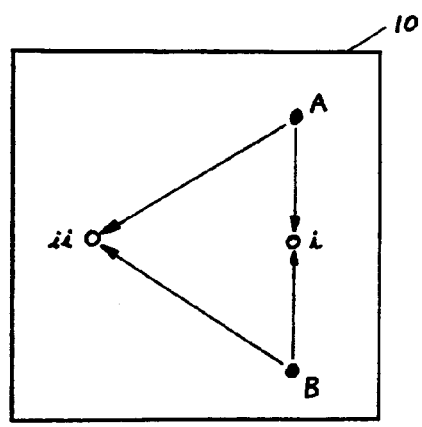
FIG. 1E shows a schematic top view of another 2×2 diffuse reflection probe preferred in the case of measurement of spectral difference in absorbance coefficient.

Next, assume that a spectral difference in absorbance coefficient, $\mu_A(\lambda_1)-\mu_A(\lambda_2)$, in bulk layer 6 was to be measured and that variations in $\mu_S$ were again considered undesired interference. In this case, a preferred arrangement of the basic 2×2 geometry is shown in FIG. 1E, where wavelength $\lambda_1$ irradiates entry point A and $\lambda_2$ irradiates B. Wavelength $\lambda_1$ is preferably chosen to be at an absorbance peak and $\mu_2$ is chosen off-peak but nearby to $\lambda_1$. Beams Aii and Bii are chosen to be transmission dominated (large lateral distance) and beams Ai and Bi are chosen to be reflection dominated (short lateral distance). Surface noise is usually dominated by Fresnel reflections, by scattering at structures larger than the measurement wavelengths, and by variations of scattering coefficient in surface layer 4 with changes in the ambient. Since all of these effects are only weakly dependent on $\lambda$, surface noise will still effectively cancel out in the ratios $TS_{ii(A)}/TS_{ii(B)}$ and $TS_{i(A)}/TS_{i(B)}$, if $\lambda_1$ and $\lambda_2$ are chosen close to each other, typically within 20%. The undesired influence of $\mu_S$ of bulk layer 6 in each ratio, $S_{Aii}/S_{Ai}$ and $S_{Bii}/S_{Bi}$, is also largely canceled out in the double-ratio, Eq.(3), and canceled the better the smaller the spectral difference is between the two scatter coefficients, $|\mu_S(\lambda_1)-\mu_S(\mu_2)|$, and the better the variations (over time) of the two track each other. Since scatter coefficients usually change slowly with $\lambda$, cancellation of scatter effects, $$\frac{\partial R}{\partial \mu_S} \cong 0,$$

is good for most types of samples and can, if necessary, be further improved by careful, experiment-based fine-tuning of the lateral distance values, as described above. On the other hand, the spectral difference in absorption, $|\mu_A(\lambda_1)-\mu_A(\lambda_2)|$, was chosen to be large so that the measured signal, $\Delta R$, is largely due to the desired $$\frac{\partial R}{\partial(\mu_A(\lambda_1)-\mu_A(\lambda_2))} \cdot \Delta(\mu_A(\lambda_1)-\mu_A(\lambda_2)).$$

In summary, the probe schematically shown in FIG. 1E can accurately measure spectral differences in absorbance coefficient. It is also a first example showing how spectrally-multivariate data (two different wavelengths) can be combined with geometrically-multivariate data (four different measurement beams) to increase the overall accuracy a.k.a. $SNR_X$ of the measurement. This last statement prepares the ground for explaining the fundamental, and so far unrecognized, $SNR_X$-advantage of multi-beam probes. All advantages mentioned so far stem from this one, fundamental advantage.

The fundamental advantage hidden in Eq.(1) is that any 2×2 probe (or higher-order probe discussed below) is guaranteed to achieve better or at least equal measurement accuracy than the corresponding 1×1 probe that would come into being by combining all its entry points into one and all its exit points into one. This is good news, e.g., for developers of advanced spectroscopic devices, but it is also contrary to common belief and practice. Common belief is that, given a fixed amount of light that can be collected back from a turbid sample, the best possible measurement accuracy is achieved by combining as much light (actually, irradiance [Watt/cm$^2$]) onto a single photodetector as possible, in order to increase that detector's "hardware-SNR." In the case of multivariate measurements, however, it is generally false to equate the (univariate) "hardware-SNR," which can be observed on an oscilloscope and typically has units of [dc-Volt/rms-Volt], with the $SNR_X$ of Eq.(2), and only the latter is directly relevant for measurement accuracy.

The fundamental advantage of multivariate over univariate measurements is that noise correlated between the different pieces of multivariate input data can be subtracted out in the measurement algorithm. The better the algorithm is at trading off, noise-subtraction versus signal-retention, the better the measurement accuracy a.k.a. $SNR_X$ will be. Accuracy is optimized when so-called multivariate Wiener filtering is used to process the multivariate input data into the single, user-desired output. For example, in spectrometry, Wiener filters can achieve high accuracy by locking in on the differences between signals at different optical wavelengths, and $SNR_X$-values achieved are often three orders of magnitude better than possible with univariate measurements. On the other hand, poorly chosen multivariate algorithms can actually perform worse than a simple univariate algorithm, or be similar in accuracy performance and thus provide no advantage for the extra hardware expense. For example, so-called pixel binning is a common procedure in spectrographs with CCD detectors and consists of averaging readouts from adjacent CCD pixels to produce a reduced number of $\lambda$-resolved bins. Binning improves the hardware-SNR per resulting bin, of course, and it can also improve the apparent end-user accuracy of the analytical result in cases where non-optimal measurement algorithms are employed. However, in all cases where optimal Wiener filter algorithms are employed, binning does not improve the measurement accuracy a.k.a. $SNR_X$, but rather decreases it, or leaves it unchanged in the best of cases. Loosely speaking, if a Wiener filter wants to average adjacent channels, then it will do so on its own. Averaging data 'manually' in advance, on the other hand, can only reduce the Wiener filter's capability to exploit the available $SNR_X$ in all directions of the multidimensional input data space. Now, the key point is, the exact same statement holds true for any kind of multivariate data, including spectrally-multivariate data, geometrically-multivariate data, and any combination of the two. The 2×2 or higher-order probe therefore takes spectrometry one step further, so to speak, by making the measurement multivariate in both optical wavelength and in beam geometry.

Graphically speaking, the only way a Wiener filter can cope with surface noise in a 1×1 spectrometric probe is to lock in on differences between signals at different wavelengths. The price paid for this, however, is reduction of the effective measurement cuvette to '$\lambda$-difference cuvette,' with small effective spectral signal. In a 2×2 probe, on the other hand, the Wiener filter can subtract out all surface noise between beams and then has the full pathlength through bulk layer 6 left, so to speak, to further maximize the $SNR_X$ between wavelengths.

The disclosed matter can thus be applied with significant benefit to a wide range of optical measurement applications. The most significant benefit is expected in two areas: (a) ill-posed measurements of small signals close to the hardware noise-floor, e.g., measurement of urea concentration in the interstitial fluid of human skin, and (b) well-posed measurements of large but spectrally-broad signals with $SNR_X$-values that can not be sufficiently improved between wavelengths alone, e.g., measurements of changes in scatter coefficient or measurements that are affected by extraordinarily large amounts of surface noise, e.g., heart rate monitoring on exercising athletes.

The fundamental advantage described above also applies to the few examples of 1×N or N×1 probes, with N>1, that have been described in the research literature. These are also guaranteed to perform better\equal than their 1×1 counterparts if optimal Wiener filter algorithms are programmed. Surface noise, however, is not effectively reduced by these probes. (Only marginal improvements are possible depending on the details of amplitude of, and possible correlation between, the surface noises underneath the different entry and exit points.) In a 2×2 or higher-order probe, on the other hand, all of the surface noise can be subtracted out, which is substantial. In fact, research groups involved in 1×N or N×1 probe designs so far have failed to realize the slight advantage in $SNR_X$ they could have gotten from an optimized measurement algorithm (Wiener filter), generally because (a) the theory behind multivariate Wiener filtering became available only recently and (b) researchers involved were mostly interested in the study of basic material properties, rather than in specific quantitative measurement applications. In other words, the optimal use of 1×N or N×1 probes (in the accuracy a.k.a. $SNR_X$ sense) is also novel. This text, however, will concentrate on 2×2 and higher-order probes because they provide substantial $SNR_X$ advantage.

Assume a hypothetical 2×2 probe where beams Ai and Bii each have 2 mm lateral distance but Aii and Bi each have 200 mm. Intuitively, one correctly concludes that this would not form a single 2×2 probe but rather two separate 1×1 probes, 200 mm apart from each other. In our terminology, the Wiener filter can no longer use signals $S_{Aii}$ and $S_{Bi}$ to subtract out noises correlated between beams, because pathlengths are so long that these signals are buried in the hardware noise floor and do not correlate with anything any more, i.e., they are not mutually-referencing with the other beams any more. In order to distinguish this probe from a true 2×2 probe, we will call this probe a "2×2/2" probe, where the last digit indicates that only two measurement beams are effectively realized. As explained above, surface noise is eliminated only in a true 2×2 probe, because at least four measurement beams are needed to establish a pair of mutually referencing beams underneath each and every entry and exit point. In the 2×2/2 probe, on the other hand, the advantage of geometrical multivariance is not realized and the probe is reduced to a repetitive sampling device, i.e., the measurement accuracy is reduced to the one that could have been achieved by just making two consecutive measurements, 200 mm apart from each other, with a single 1×1 probe. Generally speaking, and this will be discussed in detail in the discussion of higher-order probes below; in order to realize an effective, geometrically-multivariate probe, a necessary requirement is that the signals of at least a subset of the optical measurement beams are stronger than the hardware noise floor.

This concludes the discussion of FIG. 1 and the fundamental advantages of the invention. In conclusion, probe geometry can be optimized for particular applications, e.g., measurement of absorption or scattering coefficient; probe geometry can be optimized to achieve a desired effective probing depth; and multi-beam probe geometry can be combined with other modalities of measurement, e.g., spectrometry, to increase the overall accuracy a.k.a. $SNR_X$ of the measurement. (Another modality, OCT, will be described below in conjunction with FIG. 4.)

In practice, there is an important difference between the requirements for ratiometric accuracy and ratiometric stability (over time), and this difference will be discussed next. (Ratiometric accuracy will be abbreviated as r-accuracy below, in order to distinguish it from measurement accuracy a.k.a. $SNR_X$. The two are not directly related.) In many cases, only stability is required and hardware designers can take advantage of this. If the goal is r-accuracy, i.e., if the goal is to isolate and measure the spectral signature of bulk layer 6 as accurately as possible for purposes of, say, scientific study of material properties, then the contributions from the light sources, photodetectors, and surface noises must all cancel out as exactly as possible in Eq.(5), e.g., $TS_{A(ii)}(\lambda)/TS_{A(i)}(\lambda) \cong 1$, over the whole wavelength range of interest. Most practical applications, however, require only stability and then exact cancellation is not required, but rather, $TS_{A(ii)}/TS_{A(i)} \cong$ constant(time) and ditto for the other ratios in Eq.(5) is sufficient, where the magnitude of the various constants can be different from unity and different from each other.

Figure 2:
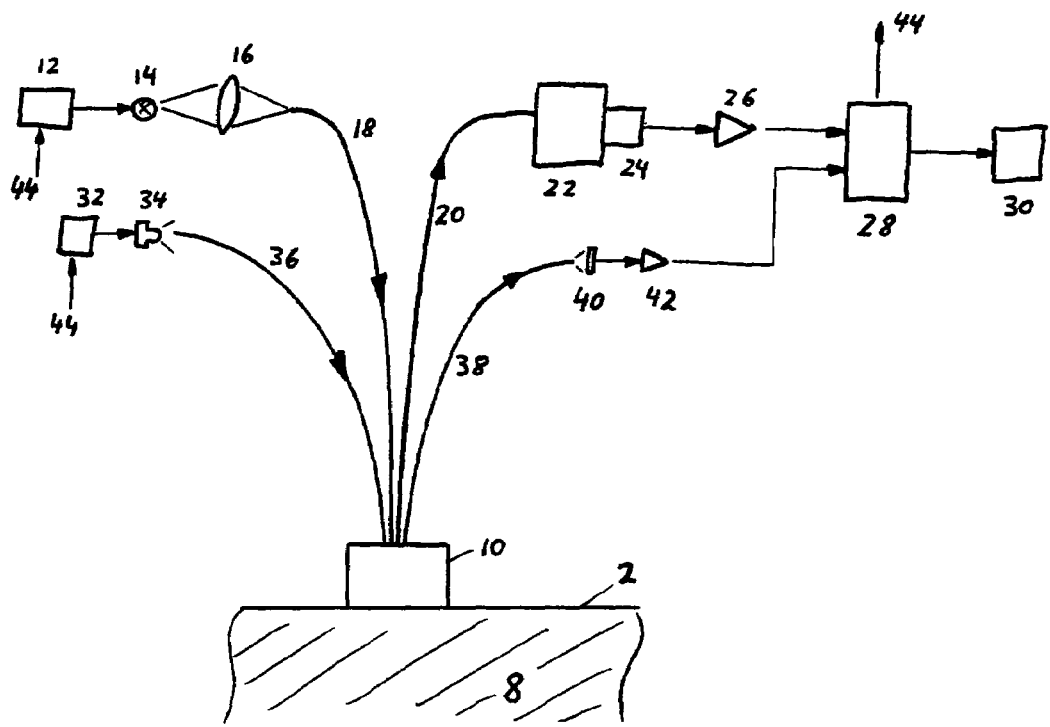
FIG. 2 shows a preferred embodiment of a diffuse reflection measurement system utilizing a 2×2 diffuse reflection probe based on optical fibers.

From a hardware point-of-view, stability is often significantly easier to achieve than r-accuracy. Consider FIG. 2, showing a preferred embodiment of an optical diffuse reflection measurement system utilizing the basic 2×2 probe geometry of, e.g., FIG. 1B. An electrical driver 12 powers a light source 14 emitting broad-band radiation covering the whole wavelength range of interest, which is collected by a lens 16 and guided through a fiber 18 to sample 8. The distal end of fiber 18 touches surface 2 of sample 8 and is therefore identical to entrance point A (not shown). Exit point ii (not shown) is formed in a similar way by the distal end of a pickup fiber 20. Fiber 20 guides the collected light to a spectrograph 22, where the light is spectrally dispersed and detected by a photodetector array 24. The electrical output signal of array 24 is amplified by a pre-amplifier 26 and fed into an electronic circuit 28 typically comprised of additional amplifiers, multiplexer, sample & hold, A/D converter, microprocessor or other digital signal processing hardware and software, and an optional user interface. According to the basic 2×2 geometry of FIG. 1B, second entry point B and exit point i (not shown) are formed by the distal ends of an illumination fiber 36 and a pickup fiber 38, respectively. Probe housing 10 hold fibers 18, 20, 36 and 38 in their designed relative positions to each other and also provides a smooth interface surface contacting sample 8.

Now, as stated above, if only stability is required then fully spectrally-resolved, canceling ratios are not absolutely necessary in Eq.(5) but rather, correlated ratios are sufficient. A cost-efficient hardware solution then is realized by illuminating fiber 36 with an LED 34 driven by an LED driver 32 and by detecting the light collected by fiber 38 with a single-element photodiode 40 and a pre-amplifier 42. Electronics 28 receives signals from preamplifiers 26 and 42, demodulates the two signals, and separately detects the four components, $S_{Aii}$, $S_{Ai}$, $S_{Bii}$, and $S_{Bi}$. Synchronous detection, e.g., using alternating pulses from light source 14 and LED 34 and gated amplifiers, or frequency modulation and lock-in amplifiers, is preferred and can be achieved by having electronics 28 provide timing signals 44 to drivers 12 and 32. LED 34 is preferably selected to emit light at a wavelength $\lambda_{LED}$ that is close to, or within, the wavelength range of interest in order to maximize the correlation between the instabilities experienced by the different optical beams. Electronics 28 computes the explicit-ratio diffuse reflection spectrum at each wavelength, $\lambda_i$, resolved by spectrograph 22 as follows:

$$R(\lambda_i) = \frac{\dfrac{S_{Aii}(\lambda_i)}{S_{Ai}}}{\dfrac{\sum_{\lambda_{LED}} S_{Bii}(\lambda_i)}{S_{Bi}}}, \quad \text{Eq. (7)}$$

where $$\sum_{\lambda_{LED}} S_{Bii}(\lambda_i)$$

indicates a sum over one or more wavelengths emitted by LED 34 and detected by spectrograph 22. Electronics 28 then applies a calibration algorithm to spectrum $R(\lambda_i)$, and then displays the measurement result on a display 30. (Various pre-processing steps known to people skilled in the art like, e.g., dark current subtraction, taking the logarithm, and mean-centering, can also be applied by electronics 28.) Since light source, photodetector, and surface instabilities are all usually dominated by spectrally-broad features that are well correlated between $\lambda_i$ and $\lambda_{LED}$, the embodiment shown in FIG. 2 is a favorable tradeoff achieving a large part of the possible stability improvement at a fraction of the cost for the fully-doubled hardware solution needed for r-accuracy, described next.

If r-accuracy is required, then fibers 18 and 36 have to be illuminated in identical ways, and light collected by fibers 20 and 38 has to be spectrally resolved, detected, and processed in identical ways. This can be achieved (not shown) by doubling elements 12, 14, 16 and 22, 24, 26 with elements 12', 14', 16' and 22', 24', 26'; and by replacing elements 32, 34 with 12', 14', 16' and elements 40, 42 with 22', 24', 26' so that both illumination fibers 18 and 36 and both detection fibers 20 and 38 are equipped with identical sets of hardware. Electronics 28 contains control circuitry to modulate light sources 14 and 14', e.g., by turning them on and off in alternating sequence.

A more economical way to achieve r-accuracy would be to use existing elements 12, 14, 16 and 22, 24, 26 twice, so to speak, by (a) adding a chopper wheel (not shown) to the illumination optics in such a way that fibers 18 and 36 are illuminated in alternating sequence by the same elements 12, 14, 16 and (b) guiding fibers 20 and 38 to the input slit of the same spectrograph 22 in such a way that fiber 20 illuminates, say, the upper half of the input slit and fiber 38 the lower half. Array 24 then needed to be a two-dimensional array with, e.g., 512×2 pixels, and spectrograph 22 would be used in an 'over-and-under' or 'semi-imaging' way, i.e., the light from fiber 20 would be detected on, say, the lower half of array 24 and the light from fiber 38 on the upper half of array 24. This system would allow to measure an r-accurate, fully spectrally resolved, double-ratio diffuse reflection spectrum by rapidly alternating the optical signal between entry points A and B (fibers 18 and 36) and measuring the output signals from exit points ii and i simultaneously (on array 24). All surface instabilities changing on time scales slower than the A-B-A-B- . . . sequence would be ratioed out.

Yet another, still more economical way to achieve r-accuracy would be to measure the signals of all four beams $S_{Aii}$, $S_{Ai}$, $S_{Bii}$, $S_{Bi}$ in an alternating time sequence, e.g., by adding a second chopper (not shown) in front of the input of spectrograph 22 in such a way that pickup fibers 20 and 38 illuminate the input slit of spectrograph 22 in an alternating way and synchronized with the first chopper wheel mentioned above, which selects between illumination fibers 18 and 36. In practice, the function of the two synchronized chopper wheels is more easily achieved by using one wheel with two different wheel patterns. This last system can significantly reduce part cost because array 24 can be one-dimensional and spectrograph 22 can be non-imaging. The tradeoff for the reduced cost is a further slight reduction in performance because less measurement time is spent per each optical beam, i.e., slightly more random noise per given total measurement time, and the time intervals between the measurement time slots of mutually-referencing beams are larger, i.e., slightly reduced stability. This concludes the discussion about the important practical difference between the requirements of ratiometric stability and r-accuracy. In summary, stability is often significantly easier and more economical to achieve in practice, and in virtually all applications a multitude of possibilities exist to trade off cost versus performance, especially when only stability is required.

Figure 3:
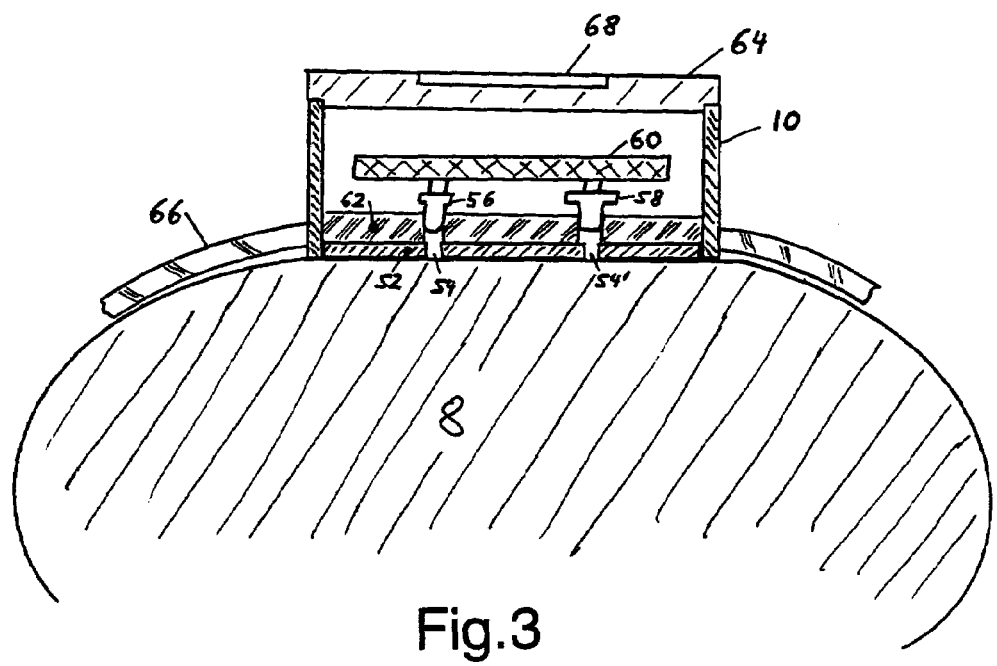
FIG. 3 shows a cross-section of a preferred embodiment of a miniaturized diffuse reflection measurement system utilizing a 2×2 or higher-order diffuse reflection probe based on LEDs and Silicon photodiodes.

The embodiment shown in FIG. 2 is preferred in low-volume applications, where high $SNR_X$ is more important than cost, e.g., many industrial process-control applications. Higher volumes justify higher development expenses, and embodiments for medium- and high-volume applications can be significantly more customized. A preferred embodiment of a low-cost, low-power, miniaturized, 2×2 or higher-order probe for medium-volume, noninvasive, biomedical applications based on discrete LEDs and Silicon photodiodes, is shown in cross-section in FIG. 3. Housing 10, which can be substantially circular in shape with a diameter preferably smaller than about 4 cm, is fixed with a bracelet 66 to sample 8, e.g., the wrist of the human arm, much like a watch. The front plate 52 is preferably optically opaque and contains precision-machined openings 54, 54' etc. that define the entry and exit points. Openings 54, 54' etc. can be filled with an optically transparent material like, e.g., Silicone, to prevent accumulation of dirt, and their diameters and relative locations can be chosen, e.g., according to one of the schematics shown in FIGS. 1B–E. A printed circuit board 60 contains at least two LEDs and at least two Silicon photodiodes, which can be discretely packaged. One LED 56 and one photodiode 58 are shown in FIG. 3. A layer of opaque rubber material 62 contains tightly fitting openings for the LEDs and silicon diodes and is used to (a) provide mechanical stability to the construction, (b) prevent light leakage from the LEDs to the photodiodes inside housing 10, and (c) help seal housing 10 from dust and other environmental stresses. Board 60 contains electronic components (not shown) that pulse the LEDs; readout the photodiodes; detect the signals of the at least four measurement beams individually; process the signals in such a way that all surface instabilities are effectively canceled out; apply an algorithm to generate the desired analytical result, preferably a Wiener filter; optionally apply further processing steps including a unit change to adjust for different user preferences in different parts of the world; and display the result on a display unit 68 located in a lid 64 of housing 10.

The LEDs are preferably pulse-modulated with a pulse frequency on the order of several kHz. Low power, quasi-continuous operation is possible by measuring intermittently, e.g., one measurement lasting 10 seconds every 5 minutes. Battery operation is possible in many applications and solar cell powering is possible in some, depending on the sampling rate and $SNR_X$ requirements of the particular application.

The embodiment in FIG. 3 is useful for medium-volume applications, say, in the range of up to several thousand units, and its main advantage is the low tooling cost afforded by the discretely packaged LEDs and photodiodes. In the case of high-volume applications, many more avenues to reduce cost and create an appealing product are possible and are known to those skilled in manufacturing engineering. For example, a high-volume probe could be comprised of LEDs and photodiodes delivered as bare dies and integrated into a printed circuit board (PCB) that would carry the electronics as well as provide other opto-mechanical functions. A particularly suitable material for the PCB is low-temperature co-fired ceramic (LTTC). An LTTC board is mechanically stable enough to be part of the package, to carry the LEDs and photodiodes, and to define the openings for the entry and exit points. The openings would preferably be realized as via-holes in the LTTC board and filled with an optically transparent material like, e.g., a sol-gel based glass, in order for the probe to provide a smooth contact surface to the arm.

Figure 4:
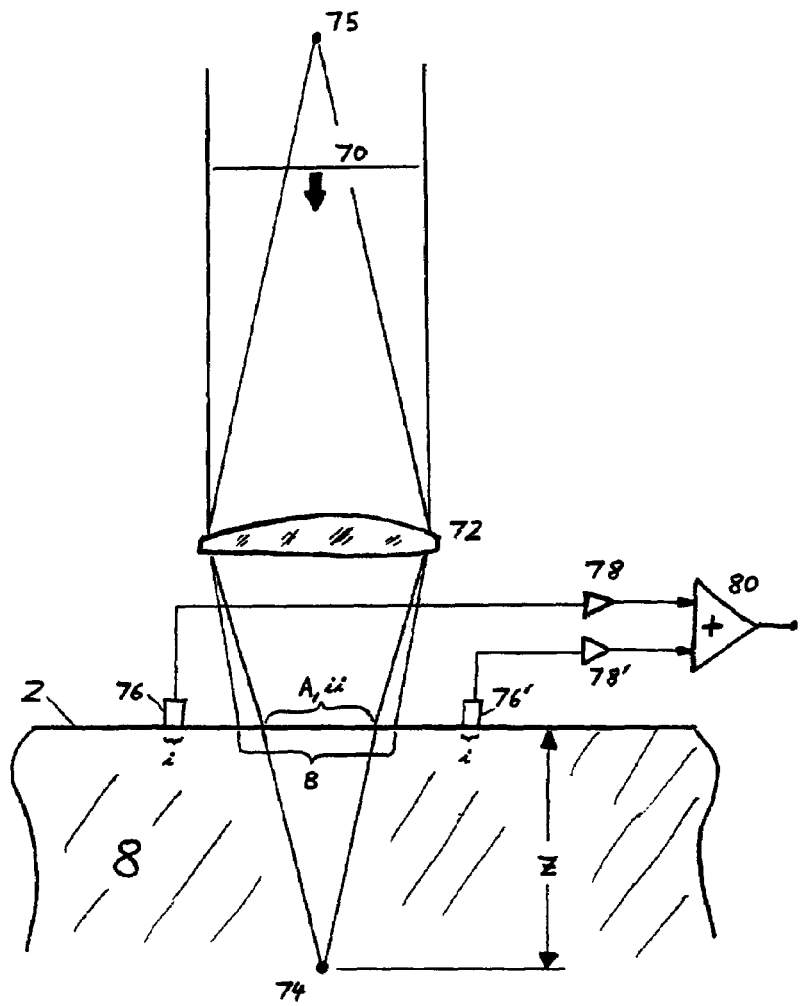
FIG. 4 shows a preferred embodiment of a 2×2 probe in an OCT measurement application.

A preferred embodiment of a non-fiber 2×2 probe for so-called optical coherence tomography (OCT) diffuse reflection is shown in FIG. 4. In a typical OCT setup, light from a superluminescent LED (SLED) is collimated and guided into a Michelson interferometer (not shown), with one output arm of the interferometer terminated by a movable reference mirror (not shown). The other output arm supplies a collimated wavefront 70 to an objective lens 72, which focuses the light into a focus point 74 inside sample 8. Both arms reflect light back into the interferometer where the two wavefronts are recombined and their energy-sum is detected by a photodetector (not shown). The focus depth (z) of objective 72 is set to a desired value and the optical length of the reference interferometer arm is adjusted by setting the position of the reference mirror, such that the interferometer is at zero-path difference with regard to point 74. The fact that illumination and pickup optics are confocal, and the coherent detection afforded by the interferometer, cause the reflected light to be preferably detected from point 74, i.e., the effective measurement cuvette through sample 8 is more or less given by a single scatter-event path: straight in, backscattered at point 74, and straight back out. Entry point A and exit point ii formed on surface 2 are thus identical. Now, in order to stabilize the measurement result, the OCT probe is extended to a 2×2 geometry by adding an LED 75 and one or more photodiodes 76, 76', etc. Photodiodes 76, 76', etc. are preferably located circularly around the optical axis of lens 72 and their output signals are amplified by pre-amps 78, 78', etc and added electrically in adding circuit 80. Exit point i thus consists of as many discrete areas as there are photodiodes 76, 76', etc. LED 75 is preferably located at a distance far enough from lens 72 such that its entry point B formed on surface 2 is only insignificantly larger than entry point A. Electronics (not shown) modulate the SLED (not shown; A) and LED 75 (B), demodulate the output signals from the detector located at the interferometer (not shown, ii) and from adder 80 (i), and compute the double-ratio as, $$R(z) = \frac{\frac{S_{Aii}(z; \lambda_{SLED})}{S_{Ai}(\lambda_{SLED})}}{\frac{S_{Bii}(\lambda_{LED})}{S_{Bi}(\lambda_{LED})}}. \qquad \text{Eq. (8)}$$

The confocality effect also applies to beam Bii, however, there will be no interference effects when detecting $S_{Bii}$ because the interferometer is (with virtual certainty) far from zero-path difference with regard to this beam. Thus, detection of optical power $S_{Bii}$ is not as concentrated around point 74 as is detection of $S_{Aii}$, and in general, $S_{Bii}$ will be detected from shallower depth. By choosing wavelengths $\lambda_{SLED}$ and $\lambda_{LED}$ to be close to each other, surface instabilities are effectively canceled out.

Figure 5A:
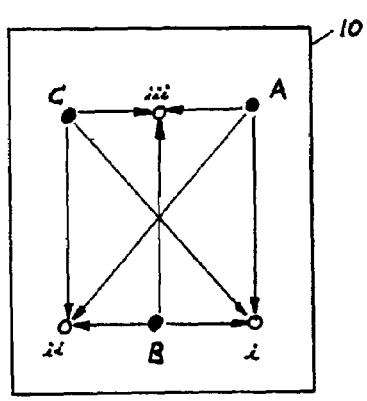
FIG. 5A shows a schematic top view of a preferred 3×3 diffuse reflection probe.

Next, we discuss higher-order probes, i.e., $N_{in} \times N_{out}$ probes with $N_{in} \geq 2$; $N_{out} \geq 2$; and $N_{in} \times N_{out} > 4$ (i.e., at least one of the two, >2). One question that immediately arises is, Why should a higher-order probe provide any additional advantage over a 2×2 probe? The answer is two-fold and important. A schematic of a preferred, particularly compact 3×3 probe is shown in FIG. 5A and will be used as an example in the following discussion. The entry and exit points in FIG. 5A can be realized by using, e.g., LEDs and photodiodes or fiber optics, as described above. The first part of the answer is that the fundamental advantage hidden in Eq.(1) applies again, i.e., the 3×3 probe of FIG. 5A is guaranteed to be better or at least equal in $SNR_X$ than any of the 2×2 probes that could be formed by co-adding some of its nine signals, into four signals, as long as optimal measurement algorithms (Wiener filters) are used. The reason for this is again given in Eq.(1), which guarantees that the higher the number of measurement beams, the better/equal the $SNR_X$. Of course, in practice the number of measurement beams is restricted by hardware cost and space limitations. Also, given that both the 2×2 and the 3×3 probe can eliminate surface noise completely, the increase in $SNR_X$ is characterized by diminishing return. Certainly, the advantage due to spatial-averaging afforded by a 3×3 probe can often be achieved more economically by just moving a 2×2 probe to different places on sample surface 2 and averaging the consecutive measurements. So the question is, where should a practically significant increase in $SNR_X$ come from? The second part of the answer is application-specific and for many applications, highly relevant. First, higher-order probes can be used in some applications to combine surface noise cancellation with other, particular measurement needs (for an example, see the discussion of FIGS. 5B–C below). Second and even more important, higher-order probes can deliver information about the spatial distribution of a property or component in a sample, e.g., a depth profile, and this information is often highly relevant for a user-desired result.

For example, in many industrial process-control applications the ability to measure the depth profile of moisture is important to fine-tune yield and quality of production processes, e.g., when making wooden boards or foodstuff. Another, particularly important biomedical application example is the measurement of the scattering coefficient, $\mu_S$, of human skin as an indicator of the blood glucose concentration. It is known that the time profile of the glucose concentration in the skin is not perfectly correlated with the one in blood. One method that has been proposed to decrease the resulting so-called tracking error, is to make several consecutive skin measurements, say, at 10 minute intervals, then from these compute the rate of change in skin glucose concentration [(mg/dL)/minute], and then from the rate of change compute a correction factor to improve the accuracy of the current blood concentration measurement result. The point is, a depth-profile measurement at a single moment in time can be used to decrease tracking error in a similar way. Best tracking is achieved when probing the skin at a depth of about 150 microns, because a dense network of capillaries is located at this depth (so-called venous plexus). Probing at other depths will yield concentration values that are relatively less well tracking with the concentration in the blood, i.e., information about the overall skin tracking error is embedded in the differences between the concentrations at different depths. Higher-order probes can use this information to improve the accuracy a.k.a. $SNR_X$ of the measurement, by subtracting out tracking-noise in the same way that the differences between mutually-referencing beams are used to cancel out surface noise, viz., by applying the Wiener-filter method of signal-processing (see below) to the output data of the higher-order probe.

Another question is, How to process the $N_{in} \times N_{out} > 4$ many, individually-detected signals of a higher-order probe in order to effectively cancel out surface noise? There are basically two methods to achieve effective cancellation underneath all entry and exit points. The so-called explicit-ratio method focuses exclusively on surface noise whereas the Wiener-filter method takes all sources of noise affecting the measurement into consideration. Both methods will be discussed separately below, although mixtures of the two can also be applied in practice.

The explicit-ratio method is basically an extension of Eq.(3) to higher-order probes, with Eq.(3) now called the fully-referenced double-ratio (FRDR) of the four beams between A, B, ii, and i; or $R_{A,B,ii,i} = (S_{Aii}/S_{Ai})/(S_{Bii}/S_{Bi})$ for short. The explicit-ratio method of processing the signals is, first, to compute at least a subset of all possible FRDR's and then, second, to use only these FRDR's as input for any subsequent processing steps. (As always, the various pre-processing steps known to those skilled in the art like, e.g., dark current subtraction, detector linearization, taking the logarithm, mean-centering, etc. can also be applied but are not discussed in detail here.) The explicit-ratio method was used in Eq.(3) and the discussion of FIGS. 1B–E above, where the basic 2×2 probe geometry yielded only a single possible FRDR. (We count the four possible double-ratios that can be formed from a set of four fully-referenced signals, e.g., $R_{A,C,iii,i} = (S_{Aiii}/S_{Ai})/(S_{Ciii}/S_{Ci})$ $R_{A,C,i,iii} = (S_{Ai}/S_{Aiii})/(S_{Ci}/S_{Ciii})$, $R_{A,C,iii,i}^{-1}$, and $R_{A,C,i,iii}^{-1}$; as one FRDR, not several.) The number of possible FR's, $\#_{FRDR}$, increases sharply with increasing order and is given by, $$\#_{FRDR} = \frac{N_{in} \cdot N_{out} \cdot (N_{in} - 1) \cdot (N_{out} - 1)}{4}. \qquad \text{Eq. (9)}$$

For example, in the 3×3 probe of FIG. 5A, there are $3 \cdot 3 \cdot 2 \cdot 2/4 = 9$ different FRDR's: $R_{A,B,ii,i} = (S_{Aii}/S_{Ai})/(S_{Bii}/S_{Bi})$, $R_{A,B,iii,i} = (S_{Aiii}/S_{Ai})/(S_{Biii}/S_{Bi})$, $R_{A,C,ii,i} = (S_{Aii}/S_{Ai})/(S_{Cii}/S_{Ci})$, etc. The explicit-ratio method computes at least a subset of the possible FRDR's, using the raw signals or some pre-processed form of the signals, e.g., logarithmized signals, $R_{A,B,ii,i} = -\log\{(S_{Aii}/S_{Ai})/(S_{Bii}/S_{Bi})\}$ etc.; and then restricts the input of any further processing, if there is any, to the results $R_{A,B,ii,i}$, $R_{A,B,iii,i}$, etc., whereas the individual signals $S_{Aii}$, $S_{Ai}$ etc. are no longer used. Advantages of the explicit-ratio method include the guaranteed, complete elimination of all surface noises; the relative ease of calibration; and the retained physical insight in the inner workings of the algorithm, which can guide optimization of probe geometry, see, e.g., the discussion of FIG. 5B below.

The Wiener filter method is to perform Wiener filtering directly on at least a subset of the individual, raw or pre-processed signals, e.g., $-\log(S_{Ai})$, $-\log(S_{Aii})$, . . . , $-\log(S_{Ax})$, $-\log(S_{Bi})$, $-\log(S_{Bii})$, . . . , $-\log(S_{Bx})$, $-\log(S_{Ci})$, . . . , etc.; thus allowing the Wiener filter to freely form, so to speak, approximate double-ratios as required to optimize the $SNR_X$ of the measurement. A brute-force approach to deriving the Wiener filter for any measurement problem is to collect a large set of so-called calibration data, comprised of optical data from the diffuse reflection probe and of so-called lab-references, i.e., the desired "true" results. The Wiener filter can then be found, basically, by correlating the optical data with the "true" data. This approach is known as "statistical modeling" by those skilled in the art and is widely used and well described in the pertinent literature.

Superior methods for determining the Wiener filter have recently been described in Marbach 2002 and in U.S. Pat. No. 6,629,041 B1, both of which are included here for reference. To summarize here shortly: First, the response vector g is determined (cmp. the discussion of Eq.(1) above; in practice, g is often known a-priori or can be determined by software simulation or by measurement of samples of known composition); and then second, the covariance matrix of the multivariate noise, $N_x$, is determined by collecting optical data using the given diffuse reflection probe in realistic conditions. The Wiener filter with unity slope is then given by, $$b = \frac{N_x^{-1} g}{g^T N_x^{-1} g}.$$

Collection of lab-reference data is no longer necessary.

The advantage of the Wiener filter method is that the overall measurement accuracy a.k.a. $SNR_X$ is optimized considering all types of measurement noises, including surface noise. Even though the Wiener filter may not get rid of 100% of the surface noise, it effectively cancels out all that surface noise that is in the way of measurement accuracy, keeping only that (small) part of the surface noise that happens to be in a data subspace with significant useful signal. For example, in the case of a 2×2 probe used in an application with dominant surface noise, the Wiener filter will be practically identical to the explicit-ratio result, Eq. (3). Depending on the details of the other noises affecting the measurement and their relative strength compared to the surface noise, there will be slight deviations, e.g., instead of the exact explicit-ratio filter, $k \cdot [+1-1-1+1]^T$ (using vector notation), the Wiener filter may be, $b = k \cdot [+1.01 -0.96 -1.03 +0.99]^T$, giving an output, $$\text{output} = k \cdot [\; -\log S_{Aii} \quad -\log S_{Ai} \quad -\log S_{Bii} \quad -\log S_{Bi} \;] \cdot \begin{bmatrix} +1.01 \\ -0.96 \\ -1.03 \\ +0.33 \end{bmatrix},$$

which is very close to the explicit-ratio result. (Above, k is an application-specific and basically arbitrary scaling factor determined, among other things, by the physical unit of the output displayed to the user; see Marbach 2002 for details.) From the point of view of hardware design and generally speaking, as long as a 2×2 or higher-order probe is designed such that surface noise can be subtracted out using the explicit-ratio method, i.e., as long as each point of light entry or exit is shared by two mutually-referencing beams, the Wiener filter method will also work, i.e., will effectively cancel surface noise.

Mixtures of the two signal-processing methods discussed above can also be used in practice. For example, a Wiener filter may be determined in the way described above and then the nearest-neighbor filter consisting of "pure" FRDR's can be selected. Or, a set of FRDR's can be computed first and then Wiener filtering can be applied to them.

An advantage of the Wiener filter method is that it seamlessly integrates multivariate data of different kinds into a single, optimal solution in a relatively straightforward way. Continuing the previous example, if the 3×3 probe of FIG. 5A is used for a spectroscopically resolved measurement of the scatter coefficient of human dermis, which then is used to predict the glucose concentration in blood, then the Wiener filter will automatically: cancel surface noise between beams, cancel spectrally interfering noise between wavelengths, and cancel tracking noise by locking in on differences in the skin glucose at different depths.

The Wiener filter method is therefore recommended for all cases where measurement accuracy is critical, including 2×2 probes or higher-order probes. A very good way of optimizing probe geometry (and all other instrument hardware, for that matter) is to build a prototype probe containing many more entry and exit points and many more spectroscopically resolved wavelengths than expected necessary in the final product; then determine the g-vector and covariance matrix, $N_x$, of the over-specified prototype probe; and then select a subset of measurement beams and optical wavelengths that provides a good tradeoff between measurement accuracy a.k.a. $SNR_X$ and hardware complexity. This procedure is extremely powerful and expedient.

Figure 5B:
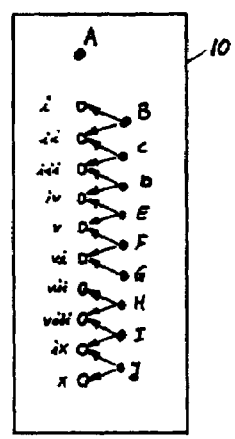
FIG. 5B shows a schematic top view of a preferred 10×10/28 probe for the stable and reproducible measurement of spatially resolved diffuse reflection.

The explicit-ratio method is recommended in cases where physical insight is important. For example, a preferred embodiment of a probe for measuring spatially resolved diffuse reflection, $R(\lambda;r)$, with r[mm] the lateral distance, is schematically shown in FIG. 5B. Entry point A and exit points i, ii, . . . , x are located within the outline of probe housing 10 and are designed to measure $R(\lambda;r)$ of a particular type of sample at ten different lateral distances. Usually, the desired measurement result is the spatial profile of diffuse reflection as determined, e.g., by the incremental ratios: $S_{Aii}/S_{Ai}$, $S_{Aiii}/S_{Aii}$, . . . , $S_{Ax}/S_{Aix}$. Surface noise is eliminated from the incremental ratios by providing entry points B, C, . . . , I, J; as shown. The location of B is chosen such that beams Bi and Bii are signal redundant, the location of C is chosen such that Ciii and Cii are signal-redundant, etc. The explicit-ratio method of signal processing is used and the incremental ratios are computed as, $(S_{Aii}/S_{Ai})/(S_{Bii}/S_{Bi})$, $(S_{Aiii}/S_{Aii})/(S_{Ciii}/S_{Cii})$, . . . , $(S_{Ax}/S_{Aix})/(S_{Jx}/S_{Jix})$. The ratios in the denominators are close to unity and do not affect the desired results; rather, they are merely used to cancel out surface noises and detector instabilities. We note that in the notation introduced above, the probe shown in FIG. 5B is called a 10×10/28 probe and not a 10×10 probe because "only" 28 out of the theoretically possible 100 measurement beams are realized. Still, surface noise is completely eliminated because each of the 28 realized beams is part of a true 2×2 probe. In the example of FIG. 5B, there are obviously nine 2×2 probes combined to form the one 10×10/28 probe, and surface noise in higher-order probes is obviously eliminated as long as the probe consists of a combination of multiple 2×2 probes.

Figure 5C:
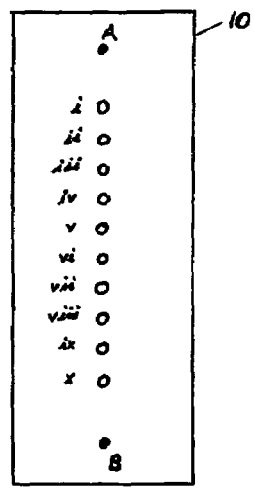
FIG. 5C shows a schematic top view of a preferred 2×10 probe for the stable and reproducible measurement of spatially resolved diffuse reflection.

Another preferred embodiment of a probe measuring $R(\lambda;r)$ is schematically shown in FIG. 5C. Entry point B is located such that beams Ai and Bx are signal-redundant, Aii and Bix are signal redundant, etc. The advantage of the 2×10 probe in FIG. 5C over the 10×10/28 probe in FIG. 5B is the potentially simpler hardware. The explicit-ratio method can still be used to compute the desired incremental ratios, but the simple one-to-one relationship to the fully-referenced double-ratios (FRDR) of FIG. 5B is lost and additional computing is necessary. First, at least a subset of the 2·10·1·9/4=45 possible FRDR's is computed and then the desired incremental ratios are computed from these FRDR's in a second step, by solving a system of equations derived from the known symmetry of the probe. For example, assuming the usual logarithmic way of pre-processing the signals, $R_{A,B,vi,v}=-\log\{(S_{Avi}/S_{Av})/(S_{Bvi}/S_{Bv})\}$ can be immediately seen to be, $R_{A,B,vi,v}=-2\times\log(S_{Avi}/S_{Av})$. Other incremental ratios can be derived in a similar way by solving a system of linear equations, e.g., $R_{A,B,ii,i}=-\log(S_{Aii}/S_{Ai})-\log(S_{Ax}/S_{Aix})$. Preferably, the equation system has more equations (FRDR's, maximal 45) than variables (incremental ratios, maximal 9) and is solved in a least-squares way, in order to take advantage of the noise averaging effects afforded in an overdetermined equation system.

The apparatus and methods disclosed are merely examples of particularly useful embodiments, and numerous modifications and variations are possible. First, the optical, mechanical, and electronic hardware involved in generating measurement light, bringing light to the sample, picking light up from the sample, and detecting the signals from the individual measurement beams; can be designed and realized in numerous different ways, especially when measurement light is also spectroscopically resolved or when other modalities of optical measurement, e.g., different light polarizations, are employed.

A multitude of modifications and variations are also possible to the diffuse reflection probe itself. For example, within a given probe, different types of components can be used to form the entry and exit points, e.g., the entry points can be realized by LEDs and the exit points can be realized by optical fibers. Also, the distance between the light-bringing components and surface 2 can be different from the distance between the light-collecting components and surface 2, and the distances can be small or large relative to the size of the optically probed sample-volume. For example, mirrors or lenses can be used to focus light onto surface 2 from a relatively large distance, and optical fibers touching surface 2 can be used to pick reflected light up. Entry and exit points can be spatially separate from each other or can be overlapping, and can be arranged on a planar surface or on a macroscopically curved surface, e.g., arranged radially like wheel spokes around a human finger. Optical measurement beams can be modulated and electrical signals be demodulated such that signals from different measurement beams are measured simultaneously or consecutively in time. Different modulation techniques, e.g., chopping and lock-in detection, can be used to separate signals detected on a single detector. These and other modifications and variations are apparent to those skilled in the art and fall within the scope of the appended claims.

I claim:

1. A 2×2 or higher-order optical probe, comprised of:
   (a) illumination means, including at least one light source, for forming at least two points of light entry into a sample;
   (b) light collection means for forming at least two points of light exit from said sample;
   (c) light modulation means for establishing at least four optical measurement beams through said sample wherein each of said points of light entry and each of said points of light exit is shared by at least two of said optical measurement beams;
   (d) detection means, including at least one photodetector, for detecting the signals of at least four of said optical measurement beams; and
   (e) signal processing means for processing said signals such that all surface instabilities are effectively canceled out.

2. The optical probe of claim 1, wherein said illumination means are comprised of LEDs located in close proximity to the surface of said sample.

3. The optical probe of claim 1, wherein said light collection means are comprised of photodetectors located in close proximity to the surface of said sample.

4. The optical probe of claim 1, wherein said illumination means and said light collection means are comprised of optical fibers butted against the surface of said sample.

5. The optical probe of claim 1, wherein said light modulation means are comprised of electronic drivers modulating said illumination means and said detection means are comprised of electronic amplifiers synchronously demodulating the output of said at least one photodetector.

6. The optical probe of claim 1, wherein said points of light entry and said points of light exit are spatially separate from each other.

7. The optical probe of claim 1, wherein at least a subset of said points of light entry and said points of light exit are spatially overlapping.

8. The optical probe of claim 1, wherein the size and relative location of said points of light entry and said points of light exit are designed to achieve a desired multivariate signal-to-noise ratio of a particular analytical measurement application.

9. The optical probe of claim 1, wherein the size and relative location of said points of light entry and said points of light exit are designed to achieve a desired effective sampling depth.

10. The optical probe of claim 1, wherein said illumination means, said light collection means, said light modulation means, and said detection means are designed to achieve ratiometric stability.

11. The optical probe of claim 1, wherein said sample is human skin.

12. A 2×2 or higher-order optical probing method, comprising the steps of:
    (a) forming at least two points of light entry and at least two points of light exit on a sample;
    (b) establishing at least four optical measurement beams through said sample wherein each of said points of light entry and each of said points of light exit is shared by at least two of said optical measurement beams;
    (c) detecting the signals of at least four of said optical measurement beams; and
    (d) processing said signals such that all surface instabilities are effectively canceled out.

13. The method of claim 12, wherein said step (d) is comprised of the explicit-ration method.

14. The method of claim 12, wherein said step (d) is comprised of the Wiener-filter method.

15. The method of claim 12, wherein said step (c) is comprise of performing a spectroscopically resolved measurement of at least one of said optical measurement beams.

16. The method of claim 12, wherein said optical measurement beams are comprised of light from the VIS and NIR wavelength ranges.

17. The method of claim 12, wherein said method is used to measure the refractive index of human skin.

18. The method of claim 12, wherein said method is used to measure the human heart rate.

19. A 2×2 or higher-order optical probing method, comprising the steps of:
    (a) probing a sample with at least four optical measurement beams;
    (b) arranging said optical measurement beams such that each point of light entry and each point of light exit is shared by at last two of said optical measurement beams;
    (c) modulating at least two of said optical measurement beams and detecting the signals of at least four of said optical measurement beams; and
    (d) processing said signals such that all surface instabilities are effectively canceled out.

20. The method of claim 19, wherein step (b) is comprised of arranging the size and relative location of said points of light entry and said points of light exit such that the three-dimensional beam overlap underneath each said point of light entry and each said point of light exit reaches a predetermined depth.

* * * * *